(12) United States Patent
Jones

(10) Patent No.: US 9,649,445 B2
(45) Date of Patent: *May 16, 2017

(54) DOSING MECHANISM FOR A DRUG DELIVERY DEVICE

(75) Inventor: Christopher Jones, Worcestershire (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 780 days.

This patent is subject to a terminal disclaimer.

(21) Appl. No.: 13/322,351

(22) PCT Filed: May 28, 2010

(86) PCT No.: PCT/EP2010/057484
§ 371 (c)(1),
(2), (4) Date: Mar. 9, 2012

(87) PCT Pub. No.: WO2010/139638
PCT Pub. Date: Dec. 9, 2010

(65) Prior Publication Data
US 2012/0165749 A1    Jun. 28, 2012

Related U.S. Application Data

(60) Provisional application No. 61/182,844, filed on Jun. 1, 2009.

(30) Foreign Application Priority Data

Jul. 10, 2009   (EP) .................................... 09009049

(51) Int. Cl.
*A61M 5/31*   (2006.01)
*A61M 5/315*   (2006.01)

(52) U.S. Cl.
CPC ...... *A61M 5/31538* (2013.01); *A61M 5/3155* (2013.01); *A61M 5/31535* (2013.01);
(Continued)

(58) Field of Classification Search
CPC .......... A61M 5/31553; A61M 5/31555; A61M 5/3155; A61M 5/31548; A61M 5/31545;
(Continued)

(56) References Cited

U.S. PATENT DOCUMENTS 2,283,915 A * 5/1942 Cole ................. A61M 5/31551
222/158
2005/0131354 A1* 6/2005 Tachikawa ........ A61M 5/31555
604/187

(Continued)

FOREIGN PATENT DOCUMENTS

DE    19730999 C1    12/1998
JP    11216181 A    8/1999
(Continued)

OTHER PUBLICATIONS

First Office Action issued by the Chinese Patent Office for Chinese Patent Application No. 201080032060.1 dated Mar. 27, 2013.
(Continued)

*Primary Examiner* — Laura Bouchelle
*Assistant Examiner* — Anh Bui
(74) *Attorney, Agent, or Firm* — McDonnell Boehnen Hulbert & Berghoff LLP

(57) ABSTRACT

A maximum settable dose feature is disclosed that is set by a user or health care professional one time that prevents future injections from exceeding the desired maximum dose. The feature includes a locking band (5) initially in an unlocked configuration, which transforms to a locked configuration when activated after setting a desired maximum dose. The feature can include a trigger mechanism (6,11) to transform the locking band (5) to the locked configuration.

15 Claims, 2 Drawing Sheets

(52) U.S. Cl.
CPC .... *A61M 5/31536* (2013.01); *A61M 5/31541* (2013.01); *A61M 5/31545* (2013.01); *A61M 5/31548* (2013.01); *A61M 5/31551* (2013.01); *A61M 5/31553* (2013.01); *A61M 5/31555* (2013.01); *A61M 5/31595* (2013.01); *A61M 2005/3154* (2013.01)

(58) Field of Classification Search
CPC .......... A61M 5/31595; A61M 5/31591; A61M 5/31538; A61M 5/31536; A61M 5/31551; A61M 5/31535; A61M 5/31541; A61M 2005/3154
See application file for complete search history.

(56) References Cited

U.S. PATENT DOCUMENTS

| | | |
|---|---|---|
| 2009/0254044 A1 | 10/2009 | Kohlbrenner et al. |
| 2009/0254049 A1* | 10/2009 | Adams .......................... 604/247 |
| 2011/0004191 A1* | 1/2011 | Jones ................ A61M 5/31538 604/506 |

FOREIGN PATENT DOCUMENTS

| | | |
|---|---|---|
| WO | 2004020028 A1 | 3/2004 |
| WO | 2006079481 A1 | 8/2006 |
| WO | 2006089767 A1 | 8/2006 |
| WO | 2008031238 A1 | 3/2008 |

OTHER PUBLICATIONS

Translation of the First Office Action issued by the Chinese Patent Office for Chinese Patent Application No. 201080032060.1 dated Mar. 27, 2013.
English Machine Translation of Japanese Patent Publication No. 11216181 A.

* cited by examiner

DOSING MECHANISM FOR A DRUG DELIVERY DEVICE

CROSS REFERENCE TO RELATED APPLICATIONS

The present application is a 35 U.S.C. 371 National Application of PCT/EP2010/057484 filed May 28, 2010, which claims priority to U.S. Provisional Patent Application No. 61/152,844, filed Jun. 1, 2009 and European Patent Application No. 09009049.9 filed Jul. 10, 2009, the entire contents of which are incorporated entirely herein by reference.

THE TECHNICAL FIELD OF THE INVENTION

The present invention relates to a dosing mechanism for a drug delivery device and a method of setting a dose.

DESCRIPTION OF RELATED ART

A number of known drug delivery devices are intended for multi-dose applications where the user can dial or set a dose prior to injection. One such settable dose injection device is a pen-type drug delivery device where a user regularly injects themselves, sometimes more than once a day. This is increasingly common among patients having diabetes where self-treatment enables such patients to conduct effective management of their disease. These pen-type injectors typically use some form of cartridge capable of delivering multiple doses of a specific type of medicine, such as human growth hormone or insulin. For a number of end users of such devices (typically patients being prescribed medicines) several injectors are needed to dispense a number of different medicaments. For example, diabetic patients may need one injection device containing long lasting insulin and a second injector containing short acting insulin. Clearly, it is important for such patients not to confuse the dose setting needed for one medicine with the dose setting needed for a different medicine. Likewise, it is highly desirable to prevent a user from administering an over dose of a medicine as this could be fatal. This is especially true for elderly patients, particularly those who are visually impaired or suffering from dementia, or children. As such, there exists a strong need to provide users of such devices with a simple and clear means to permanently set an maximum individually settable dose so that each subsequent injection will not exceed that preset individual dose. There is also a need to provide a user with a means to set the same dose for each injection by providing a secure stop that is readily apparent to the user when a dose is being set.

Hence, it is the object of the present invention to provide a dosing mechanism which improves the known dosing mechanism of a drug delivery device with regard to above needs. Further, the object of the present invention is to specify a respective method of setting a dose.

The invention solves the above-described problems by providing a maximum settable dose feature of a dosing mechanism and a respective dosing mechanism described below that can be used in multi-dose injection devices, where the patient or a health care professional can set and then activate or trigger the maximum dose before the first injection is made. Further the above object is solved by a method of setting a permanent maximum settable dose feature. The details and the advantages of the invention will become evident from the following more detailed description of the invention.

SUMMARY OF THE INVENTION

The maximum settable dose feature of the invention can be used on practically any drug delivery device that is designed to deliver multi-doses. A particularly preferred type of delivery device is a pen-type injector where a user can set a dose before each injection by causing a rotation or linear movement of a dose setting component. The specific design of the dose setting component is not critical to the invention provided that this component in some manner initially causes the locking band of the invention to move to a position within the device that represents an initial set dose or the desired maximum settable dose. Once the locking band reaches this position, then a reversal of the motion of the dose setting component (rotational or linear) will cause the locking band to transition from an unlocked configuration to a locked configuration.

In one embodiment of the invention the maximum dose setting feature involves a combination of a movable dose setting component and a locking band, where the band has an unlocked configuration in rotational or linear engagement with the dose setting component and a locked configuration that provides a permanent stop for the dose setting component during subsequent dose setting. The locking band transitions from the unlocked to the locked configuration after a first dose is set when the motion of the dose setting component is reversed. In an alternate embodiment, the locking band transitions to the locked configuration when the user activates a trigger mechanism, such as set pin, button, pull cord, latch or equivalent triggering mechanism.

A preferred configuration of the locking band is a circular or oblong sleeve-like structure. Preferably, it is positioned over a stationary part of the device and can move linearly or rotationally with respect to that stationary part when the dose setting component is moved during the setting of a first dose. In the unlocked configuration, the band is in an expanded state, for example the band has a greater diameter, so that it does not frictionally engage the stationary part of the device that it is positioned on. In the locked configuration the band is contracted so that it frictionally engages the stationary part and is prevented from moving with respect to the dose setting component.

A variety of methods and designs are possible for ensuring that the locking band is initially in the unlocked configuration. A preferred design is where the locking band has a spring finger, a leading edge and a trailing edge. The spring finger biases the leading edge away from the inner body when the locking band is in the first unlocked configuration. The trailing edge of the locking band grips the inner body when the locking band is in the second locked configuration. Alternatively, the band can be biased in the expanded or unlocked configuration by a shim, spacer, blank, pin, or other like biasing part that is directly or indirectly connected to the trigger mechanism, such that, when the user activates the trigger mechanism the band transitions to the locked configuration. A preferred biasing part is a spacer or pin connected to a pull ring that the user pulls out of the device after the first or maximum dose is set.

Yet another embodiment of or invention is an irreversible locking mechanism for setting a maximum dose of the dosing mechanism for a drug delivery device comprising, in combination, an inner body having a distal end, a proximal end and a helical grove positioned along its axis from the proximal end to the distal end and a rotatable number sleeve. A threaded collar is attached to the number sleeve that rotates with number sleeve about the helical grove of the inner body. A locking band is positioned on the inner body having a first unlocked configuration and a second locked configuration. The locking band transitions from the first to the second configuration after a first dose is set.

The invention also covers a method for setting a maximum dose, preferably a permanent maximum settable dose, in a drug delivery device. The method comprises rotating and/or pulling a dose setting component to set a first initial dose, which will thereafter correspond to the maximum settable dose for all future injections. When the dose setting component is moved to set the first dose, the locking band, in its unlocked position, is also caused to move to a position corresponding to this first or maximum dose. Like the dose setting component, the band can be moved in a linear or rotational motion because of its engagement with the dose setting component. Once the initial dose is set, the user stops the rotation or linear movement of the dose setting component and reverses the movement of the dose setting component to cause the locking band to transition from the unlocked to the locked configuration. Alternatively, after setting the initial dose the user can activate a trigger mechanism to transform the locking band from the unlocked configuration to the locked configuration. The locking band now acts as a rotational or linear stop to prevent the user from setting a subsequent dose larger than the first initial dose set.

The term "drug delivery device" according to instant invention shall mean a multi-dose, disposable or re-useable device designed to dispense a selected dose of a medicinal product, in particular multiple selected doses, e.g. insulin, growth hormones, low molecular weight heparins, and their analogues and/or derivatives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism both comprising the mechanical parts described in this invention. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The terms "drug" or "medicinal product" or "medicament", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2, des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The term "engaged" according to instant invention shall particularly mean the interlocking of two or more components of the drive mechanism/drug delivery device, e.g. a spline, thread, or meshed teeth connection, preferably the interlocking of helical grooves or threads of components ("rotationally engaged" or "threadedly engaged").

The term "first end" according to instant invention shall mean the proximal end. The proximal end of the device or a component of the device shall mean the end, which is closest to the dispensing end of the device. The term "second end" according to instant invention shall mean the distal end. The distal end of the device or a component of the device shall mean the end, which is furthest away from the dispensing end of the device.

BRIEF DESCRIPTION OF THE DRAWINGS

Without any limitation, the invention will be explained in greater detail below in connection with preferred embodiments and with reference to the drawings in which.

DETAILED DESCRIPTION OF THE EMBODIMENTS

Figure 1:
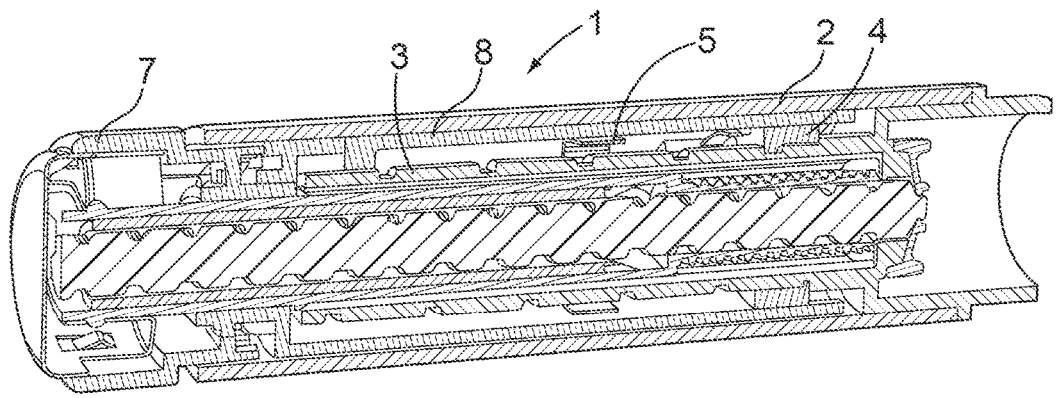
FIG. 1 shows a side sectional view of one embodiment of the inventive dosing mechanism where the locking band is positioned on a stationary part of the device.

Referring first to FIG. 1 there is shown a cross-sectional view of a dosing mechanism 1 for a pen-type injection device. As stated earlier, the maximum settable dose feature can be used with any number of multi-dose injection devices that allow a user to set a dose before each new injection. For illustrative purposes, the pen-type device shown in FIG. 1 has an outer housing 2 and an inner stationary body 3. The locking band 5 in this embodiment is shown as a tubular or ring shaped component positioned on the stationary inner body 3 in an expanded unlocked configuration. In the unlocked configuration the locking band is rotationally engaged with threaded collar 4 that is threadedly engaged to stationary body 3.

The locking band 5 may be fabricated from metal or any other durable material that is capable of gripping the stationary body 3 when the locking band 5 is in the contracted or locked configuration such that it acts as a rotational or linear stop during dose setting. For embodiments described below, the locking band 5 is illustrated as a metal pressing which grips the surface of a stationary body 3 to produce a frictional interface between the relatively soft plastic material of the inner body 3 and the relatively hard sharp edge of the metal locking band 5. This type of friction mechanism has the advantage of being settable in infinite rotational and angular positions. The geometry of the locking band 5 could be such that the higher the force exerted upon it by the dose setting component, the higher the gripping force it exerts on the stationary body 3 of the injection device. Alternatively, the locking band 5 could be fabricated as a plastic molding with a spline or tooth feature that engages with corresponding features on the stationary body 3.

Figure 2:
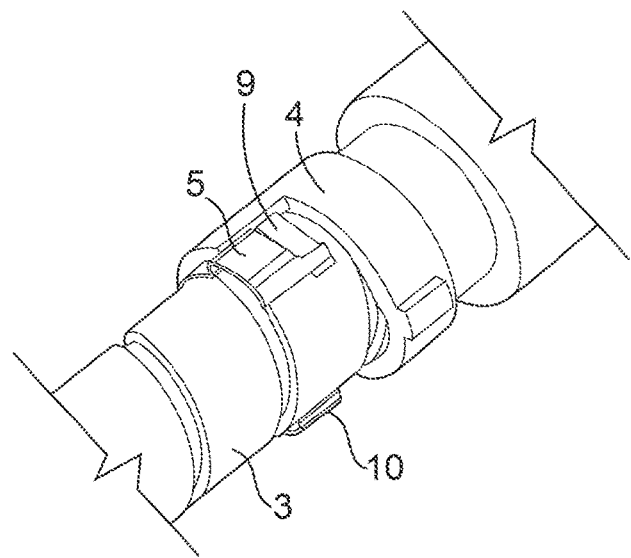
FIG. 2 shows a close up perspective view of the embodiment of the inventive dosing mechanism shown in FIG. 1 with the inventive maximum settable dose feature.

Preferably, during assembly of the injection device, the maximum settable dose feature is assembled with the locking band 5 expanded and free to move relative to the stationary body 3. This can be accomplished by using a spring finger 9 to lift the leading edge 15 of the locking band 5 and hold it in the expanded state as shown in FIG. 2. For this embodiment the spring finger 9 is a combined feature of the threaded collar 4. In the embodiment shown the trailing edge 10 grips or at least is in contact with the inner body 3 before the locking band 5 is in its fully locked configuration. It is able to rotate around the inner body 3 during the first dose setting because the self-locking geometry only works in the dial in direction. The threaded collar 4 can be considered a dose setting component for the purposes of this embodiment, however, those skilled in the art will appreciate that number sleeve 8 or dose setting knob 7 could equivalently be referred to as a dose setting component. Indeed, any component of the injection device that moves (linearly or rotationally) during the setting of a first dose and that causes (directly or indirectly) the locking band 5 to move (linearly or rotationally) to a position corresponding to a desired maximum settable dose is referred to as dose setting component. In the embodiment shown in FIGS. 1 and 2 the threaded collar 4 moves exactly with the number sleeve 8 because it is fixed both axially and rotationally to the number sleeve 8.

Figure 3:
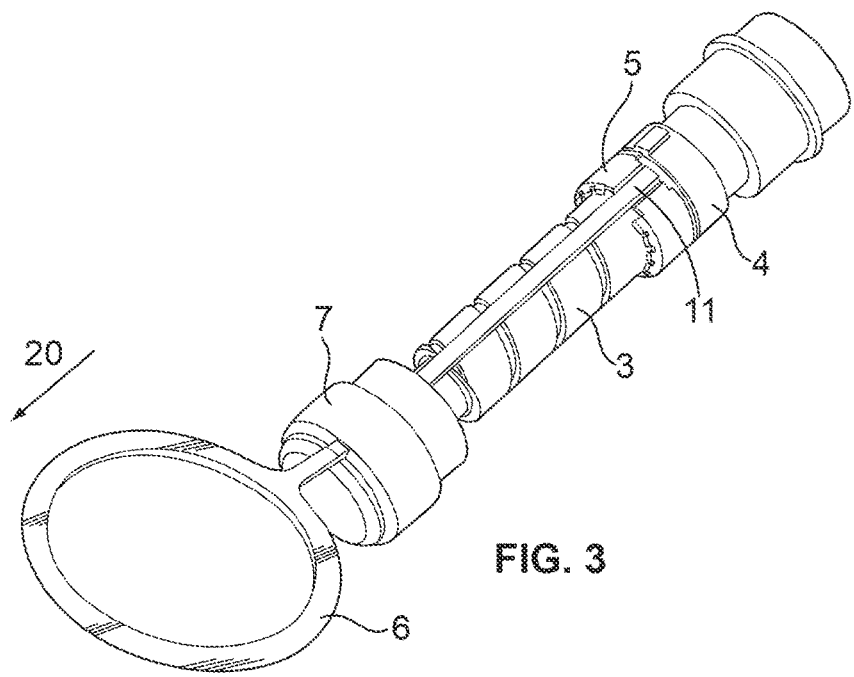
FIG. 3 shows a perspective view of another embodiment of the inventive maximum settable dose feature where a trigger is used to maintain the locking band in an unlocked configuration.

To set a dose, the user will turn dose setting knob 7, which in turn will rotate the number sleeve 8 that will turn threaded collar 4, which, because it is threadedly engaged to stationary body 3, will translate in the proximal direction (see direction arrow 20 in FIG. 3). As such, when a dose is being set, the threaded collar 4 travels along the helix of the inner body 3 carrying the locking band 5 with it. Spring finger 9 holds the leading edge of the locking band 5 away from the shank of the stationary inner body 3 preventing locking between the two components. When the desired dose size is reached the user pushes or rotates the dose setting component inwards. In the case of the embodiment shown in the Figures, the user rotates dose setting knob 7 in the opposite direction used to set the dose. In dialling down the direction of rotation of the threaded collar 4 combines with the self locking geometry of the trailing edge 10 of the locking band 5 causing the locking band 5 to grip or frictionally engage with the inner body 3 preventing the locking band 5 from rotating and thus causing it to become separated from the threaded collar 4. In detail, the spring finger 9 accommodated on the leading edge of the locking band is forced to release from under the locking band 5, preferably by a force applied by a leading edge of the collar 4 abutting upon the step-like structure 29 of the spring finger 9 and the step-like structure 25 of locking band 5. When separated from the threaded collar 4 the locking band 5 contracts and irreversibly engages the inner body 3 (see FIG. 2a) in particular with its leading edge 15 and its trailing edge 10. The locking band 5 is now in the locked configuration and acts as a stop corresponding to the selected maximum settable dose with its step-like structure 25 and the step-like structure 29 of the released spring finger 9. In this condition the locking band cannot 5 rotate in either the inward or outward direction. Thus when the user sets subsequent doses the threaded collar 4 will come into contact with the stationary locking band 5 acting as a hard stop at a dose equal to the maximum dose set initially. The stationary locking band 5 prevents the dose setting component, i.e. the threaded collar 4, the number sleeve 8 or the dose setting knob, from rotating beyond the maximum dose position that it defines.

Referring now to FIG. 3 there is shown another embodiment of the inventive maximum settable dose feature that can be used on any number of known multi-dose injection devices. For illustrative purposes, the same injection device or dosing mechanism design as shown in FIGS. 1 and 2 is presented. In this embodiment a trigger mechanism or setting pin shown as a combination pull ring 6 and biasing member 11, wherein the pull ring is accommodated at the proximal end of the biasing member 11. The biasing member is formed as a flat bar connected with its distal end to the locking band 5 in the unlocked configuration. The locking band 5 is held in its expanded condition by biasing member 11 so that the diameter of the locking band 5 is enlarged by the thickness of the biasing member 11. With the setting pin in place the locking band 5 is in its unlocked configuration where it is expanded and free to move (rotationally or linearly) back and forth relative to inner body 3 with at least one of the dose setting component, i.e. the threaded collar 4, the number sleeve 8 or the dose setting knob. Preferably, the injection device is assembled with the trigger in place. When the user dials the first dose with the setting pin in place, the locking band 5 is free to move back and forth with the dose setting component to a position corresponding to the desired maximum settable dose for all future injections.

Figure 4:
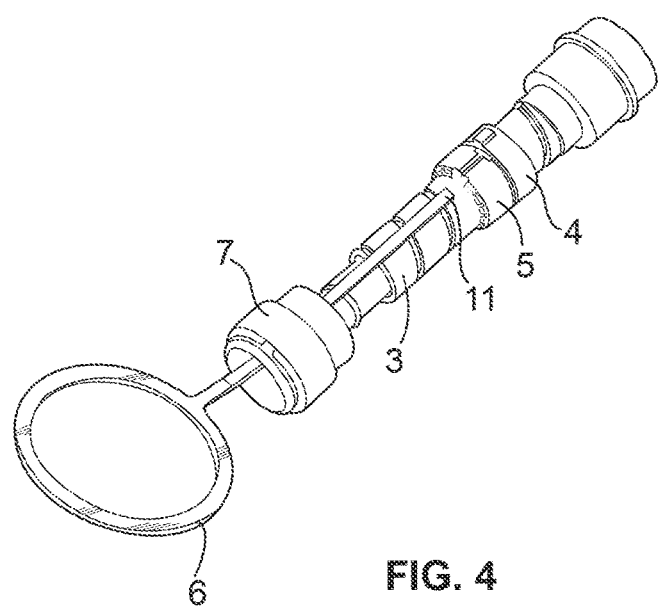
FIG. 4 shows a perspective view of the embodiment of FIG. 3 where the trigger has been activated and the locking band is in the locked configuration.

Once this maximum settable dose is reached, the trigger is activated, or in the case of the embodiment shown in FIG. 3, the pull ring 6 is pulled in the proximal direction 20 as shown in FIG. 4. This causes the biasing member to disengage from the locking band 5, which causes it to contract and transform into the locked configuration. In this condition the locking band 5 cannot rotate or move axially relative to the inner body 3 because the teeth 35 surrounding the locking band grip into the surface of the inner body 3. Thus when the device is next dialled outward the threaded collar 4/number sleeve 8 contacts the locking band 5 and is stopped and prevented from rotating beyond the maximum dose size position.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

The means, materials, and steps for carrying out various disclosed functions may take a variety of alternative forms without departing from the invention. Thus, the expressions "means to . . . " and "means for . . . ", or any method step language as may be found in the specification above or the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation within the terms of the following claims.

The invention claimed is:

1. A maximum settable dose feature of a dosing mechanism for a drug delivery device comprising, in combination,
   a. a rotating dose setting component; and
   b. a locking band having an unlocked configuration and a locked configuration,
   wherein, in the unlocked configuration, the locking band is in at least one of rotational or linear engagement with the dose setting component such that rotational movement of the dose setting component causes at least one of rotational or linear movement of the locking band,
   wherein, in the locked configuration, the locking band is separated from the dose setting component and provides a permanent stop against movement of the dose setting component in at least one direction;
   wherein the locking band transitions from the unlocked to the locked configuration after a first dose is set,
   wherein the locking band has a greater diameter in the unlocked configuration than when in the locked configuration.

2. The maximum settable dose feature of claim 1 wherein the locking band has a leading edge and a trailing edge and engages with a spring finger, wherein the spring finger holds one or both edges of the locking band in the unlocked configuration prior to setting of the first dose.

3. The maximum settable dose feature of claim 1 further comprising a release trigger that maintains the locking band in the unlocked configuration and wherein the locking band transitions from the unlocked to the locked configuration after a first dose is set when a user activates the trigger.

4. The maximum settable dose feature of claim 3, wherein the trigger comprises an elongated member having a distal end and a proximal end, where the distal end is in compression engagement with the locking band in the unlocked configuration and the proximal end is exposed to the user for grasping and activating the trigger, wherein the proximal end of the trigger comprises a pull ring for grasping by the user.

5. A dosing mechanism for a drug delivery device comprising:
   a. an inner body having a distal end, a proximal end and a helical grove positioned along its axis from the proximal end to the distal end;
   b. a rotatable number sleeve on the inner body;
   c. a threaded collar attached to the number sleeve that rotates with the number sleeve about the helical grove of the inner body;
   d. a maximum settable dose feature comprising
      a rotating dose setting component; and
      a locking band having an unlocked configuration and a locked configuration,
   wherein, in the unlocked configuration, the locking band is in at least one of rotational or linear engagement with the dose setting component such that rotational movement of the dose setting component causes at least one of rotational or linear movement of the locking band,
   wherein, in the locked configuration, the locking band is separated from the dose setting component and provides a permanent stop against movement of the dose setting component in at least one direction;
   wherein the locking band transitions from the unlocked to the locked configuration after a first dose is set,
   wherein the locking band has a greater diameter in the unlocked configuration than when in the locked configuration
   wherein the dose setting component and the locking band are on the inner body, wherein the number sleeve is the movable dose setting component.

6. The dosing mechanism of claim 5 where a spring finger biases a leading edge of the locking band away from the inner body when the locking band is in the unlocked configuration.

7. The dosing mechanism of claim 5 where a trailing edge and/or a leading edge of the locking band grips the inner body when the locking band is in the locked configuration.

8. The locking mechanism of claim 5 where, in the unlocked configuration, the locking band is rotatably engaged by the threaded collar and is free to rotate about the inner body.

9. The dosing mechanism of claim 5 where the locking band is disengaged from the threaded collar after a first dose is set and is irreversibly locked to the inner body.

10. The dosing mechanism of claim 5 wherein the locking band in the locked configuration is a dose stop defining a maximum settable dose that engages the threaded collar during setting of a second dose.

11. A method of setting a permanent maximum settable dose in a drug delivery device having,
   a. a maximum settable dose feature comprising
      a rotating dose setting component; and
      a locking band having an unlocked configuration and a locked configuration,
      wherein, in the unlocked configuration, the locking band is in at least one of rotational or linear engagement with the dose setting component such that rotational movement of the dose setting component causes at least one of rotational or linear movement of the locking band,
      wherein, in the locked configuration, the locking band is separated from the dose setting component and provides a permanent stop against movement of the dose setting component in at least one direction;
      wherein the locking band transitions from the unlocked to the locked configuration after a first dose is set,
      wherein the locking band has a greater diameter in the unlocked configuration than when in the locked configuration,
   the method comprises,
   b. rotating or pulling the dose setting component to set a first dose;
   c. rotating or pulling the locking band in the unlocked position while in rotational or linear engagement with the dose setting component;
   d. stopping rotation or linear movement of the dose setting component when the first dose is reached; and
   e. movement, preferably reversing rotation or reverse linear movement, of the dose setting component causing the locking band to transition from the unlocked to the locked configuration or activation of a release trigger, wherein the locking band transitions from the unlocked to the locked configuration when a user activates the trigger.

12. The method of claim 11, wherein
a. a dosing mechanism comprising;
   an inner body having a distal end, a proximal end and a helical grove positioned along its axis from the proximal end to the distal end;
   a rotatable number sleeve on the inner body;
   a threaded collar attached to the number sleeve that rotates with the number sleeve about the helical grove of the inner body;
   wherein the dose setting component and the locking band are on the inner body, wherein the number sleeve is the movable dose setting component
the method comprises,
b. rotating the number sleeve to set a first dose;
c. rotating the threaded collar with the number sleeve during setting of the first dose, where the threaded collar and number sleeve move in the proximal direction with the threaded collar engaging the helical grove of the inner body;
d. rotating the locking band in the unlocked position while in rotational engagement with the threaded collar;
e. stopping rotation of the number sleeve when the first dose is reached; and
f. reversing rotation of the number sleeve causing the threaded collar to move distally along the helical grove of the inner body and to disengage from the locking band causing the locking band to irreversible engage the inner body.

13. The method of claim 12 where the locking band has a leading edge and a trailing edge and engages with a spring finger, and rotating the threaded collar in a distal direction causes the spring finger to release a biasing force on the leading edge and contracting the locking band to irreversibly engage the inner body.

14. The method of claim 11 wherein a user pulls the trigger causing the locking band to transition from the unlocked to the locked configuration where it irreversibly engages the inner body.

15. A drug delivery device comprising a dosing mechanism with a maximum settable dose feature according to claim 1 and a medicament cartridge.

* * * * *